United States Patent [19]

Mercado et al.

[11] Patent Number: 4,474,772

[45] Date of Patent: Oct. 2, 1984

[54] LYSIS OF TRYPANOSOMA CRUZI

[75] Inventors: Teresa I. Mercado, Bethesda, Md.; Alba Colon-Whitt, Arlington, Va.

[73] Assignee: The United States of America as represented by the Department of Health and Human Services, Washington, D.C.

[21] Appl. No.: 375,553

[22] Filed: May 6, 1982

[51] Int. Cl.³ .............................................. A61K 35/78
[52] U.S. Cl. .................................................... 424/195
[58] Field of Search ............................... 424/195, 115

[56] References Cited
PUBLICATIONS

Merck Manual 12th ed. 1972, Trypanosomasis pp. 200-201.

*Primary Examiner*—Jerome D. Goldberg
*Assistant Examiner*—John W. Rollins
*Attorney, Agent, or Firm*—John S. Roberts, Jr.

[57] ABSTRACT

*Trypanosoma cruzi*, a protozoan parasite and the causative agent of Chagas' disease (producing chronic symptoms such as cardiomyopathy with heart failure and arrythmia), are lysed within 24 hours by an extracellular substance produced by *Pseudomonas fluorescens*. This substance, antitrypanosome factor (ATF-II) of a molecular weight approximately 1,000, actively kills the parasites at doses not toxic on mammals such as mice.

4 Claims, No Drawings

LYSIS OF TRYPANOSOMA CRUZI

This invention relates to *Trypanosoma cruzi* parasites, the cause of Chagas' disease (whose chronic symptoms are cardiomyopathy with heart failure and arrythmia), which are lysed within 24 hours by an extracellular substance produced by *Pseudomonas fluorescens*. This substance, anti-trypanosome factor (ATF-II) of a molecular weight approximately 1,000, actively kills the parasites at doses not toxic to mammals such as mice.

UTILITY STATEMENT

The ATF-II substance or factor is a most effective factor in controlling experimental Chagas' disease in mice. In vitro tests of human, horse, rabbit, sheep and mouse blood showed no hemolytic effect of ATF-II. It also did not show proteolytic activity and produced significant decreases in parasitemia.

PRIOR ART STATEMENT

Mercado, Teresa I. and Alba Colon-Whitt, "Lysis of *Trypanosoma cruzi* by *Pseudomonas fluorescens,*" (unpublished).

FLOW DIAGRAM

The flow diagram shows the step-by-step preparation of the anti-trypanosome factor.

*Pseudomonas fluorescens*

Maintained on nutrient agar slants at 4° C.

↓

8 Nutrient agar slants (one loopfull), 24 hrs., 26° C.

↓

Medium - 8 flasks (100 ml each) with 2 ml of nutrient broth wash of slants, 24 hrs., 26° C., constant shaking

↓

Medium (7 liters), each with 100 ml of 24-hr. culture, 16 hrs., 26° C., constant shaking*

↓ 2,000 g, 10 min.

Cells washed 3X, resuspended in secretion medium (200 ml) for 4½ hrs., 26° C., constant shaking**

↓ 2,000 g, 10 min.

Supernatant filtered through Millipore (0.45 μm), lyophilized and reconstituted in distilled water***

Dialysis (distilled water) 3 (500 ml) washed, Spectrapor membrane tubing (6–8,000 molecular weight cut-off)

Fraction I Lyophilized and transferred to Sephadex G-50 ($V_t$ = 159 ml) at 26° C.

Dialysates (Fractions II and III), lyophilized, dialyzed (1,000 molecular weight cut-off).

-continued

*Pseudomonas fluorescens*

Resulting dialysates desalted through Sephadex G-10 ($V_t$ = 46 ml) at 26° C.

* = OD of 100 KU (Klett-Summerson Photoelectric Colorimeter, 540 nm)
** = OD of 645 KU
*** = 10% of original volume

Background

*Pseudomonas fluorescens* is a saprophytic bacterium occurring in soil and commonly found as a contaminant of water, milk, and other refrigerated dairy products. It is psychrophilic and grows best at room temperature, approximately 26° C. Gel filtration and polyacrylamide gel electrophoresis discloses the existence of two main fractions of ATF, anti-trypanosome factor, the extra cellular substance produced by *P. fluorescens.* ATF-I, with a molecular weight greater than 20,000, is distinctly less active than ATF-II and is toxic to mice. ATF-II is a considerably smaller molecule (approximately 1,000 m.w.) and easily tolerated by mice. ATF-II attacks the posterior end of *Trypanosoma cruzi,* immobilizes and changes the trypanosomes into bizarre shapes and significantly reduced sizes.

Chagas' disease is caused by trypomastigotes of *Trypanosoma cruzi,* a parasite common to the Western hemisphere which affects children and young adults. The acute disease is characterized by fever, edema, exanthemas, and cardiomyopathy with heart failure.

The teachings of this invention show that ATF-II is a most effective factor for controlling Chagas' disease in mice by lysing *T. cruzi* through injecting processed supernatants of *P. fluorescens* intramuscularly. In the presence of ATF-II, trypomastigotes of *T. cruzi* are immobilized and disintegrated within 12 hours.

SPECIFIC DESCRIPTION OF THE INVENTION

Parasite strain. The Tulahuen strain of *Trypanosoma cruzi* is maintained by intraperitoneal inoculation of 16–20 g male mice. The infection becomes acute after 6 days, producing marked pathology of the liver and spleen.

Preparation of the Anti-Trypanosome Factor (ATF). *Pseudomonas fluorescens* bacteria are maintained in nutrient agar slants at 4° C. The factor is produced according to the scheme shown in the flow diagram above. Fractionating the supernatants produces two types of ATF: ATF-1, with a molecular weight greater than 20,000; and ATF-II, with a molecular weight of approximately 1,000. ATF-I proved quite toxic to mice in in vivo experiments; ATF-II, however, was easily tolerated, and in in vitro experiments, lysed most parasites within 24 hours. See Example 1 for more complete description of materials and methods.

Dosage and Composition. The dosage of ATF-II is 100–600 ug ATF-II protein suspended in a pharmacologically acceptable buffer. This range covers both in vitro and in vivo testing. In in vitro tests, the lower ranges are preferred; in in vivo tests, as much as 600 μg is administered daily. The preferred dosage is 180 μg ATF-II protein suspended in the buffer solution. 50 μg/ml gentamycin is added to prevent contamination of the samples. The active ingredient preferably utilizes a buffered distilled water base with gentamycin added to prevent contamination of the samples. In testing in vitro, the active ingredient is added to a buffered distilled water medium (in buffer) which contains *T. cruzi*. When in vivo use is contemplated, the active ingredient in buffer is injected intramuscularly into a mouse. Buffered DI water is preferred as a medium or carrier. It is necessary that a buffer is used and such buffer may be a mixture of sodium chloride and sodium mono- and di-phosphate (pH 8). The preferred route of use is intramuscular by injection.

Properties. Preliminary studies indicate that the ATF-I and II are resistant to heat (boiling for 5 minutes) and freezing (−20° C.). At a concentration equivalent to 1 mg/ml of protein, they were not inhibited by trypsin (5 μg, pH 8.0) but were suppressed by pronase (20 μg, pH 7.4) after 1 hour. No hemolysis was produced by either non-proteoytic fraction and they were non-proteoytic (100 ug of protein in the assay). The Lumulus amoebocyte lysate test for endotoxin revealed the presence of $1.25 \times 10^6$ ng/ml of LPS in fraction I and $1.25 \times 10^5$ ng/ml in fraction II. The presence of LPS, however, did not appear to be related to the lytic effect on the parasites since fraction I, which contained 10 times more LPS than fraction II, exhibited a much lower activity in assays against the parasite. In addition, supernatant fluids obtained after sonication of the bacterial cells did not enhance the lytic effect observed with the factor secreted extracellularly.

In Vivo Studies. Trypomastigotes of *Trypanosoma cruzi*, the causative agent of Chagas' disease, isolated from the blood of infected mice, were lysed within 24 hours by an extracellular factor from *Pseudomonas fluorescence*. Two active fractions were obtained from crude bacterial filtrates by means of gel filtration. These differed in molecular weight and extent of lytic activity. They were resistant to heat and freezing, were not hemolytic or proteolytic, were not inhibited by trypsin but were suppressed by pronase. In vivo studies indicated a protective effect against the progression of the parasitemia in mice treated with the anti-trypanosomal factor. The marked parasite multiplication and necrotic tissue changes occurring during this infection were absent also in treated animals which recovered from the infection. It has been known for many years that the fluorescent pseudomonads produce secondary metabolites possessing antibiotic activity. Such antibiotic activity has not been tested against trypanosomes.

EXAMPLE 1

Parasites. The Tulahuen strain of *Trypanosoma cruzi* was maintained by blood-passaging every 6 days in 16-20-gram male mice; 4 to 5 million trypomastigotes were usually inoculated intraperitoneally. The infection became acute after 6 days, producing marked pathology of liver and spleen, and blood counts of $1 \times 10^8$ parasites/ml were often obtained. The animals were not immunosuppressed. Blood samples were obtained under ether anesthesia directly from the heart after exposure of the cardiac surface. Parasites were isolated from blood by a two-step procedure involving separation of the red cells with lymphoprep (9.6 sodium-n-methyl-3,5 diacetamido-2-4-6, triiodobenzoate and 5.5% Ficoll; specific gravity 1.077), and elution through a DEAE-cellulose column to remove white cells and platelets. The eluted flagellates exhibited the usual lanceolate shape, were actively motile, and elicited typical infections. Two myotropic strains of *T. cruzi*, the House 510 and the House 11, of Costa Rican and Nicaraguan origin, respectively, trypomastigotes of *T. rhodesiense*, strain 1886, and *T. equiperdum*, and promastigotes of *Leishmania brasiliensis* were used also.

Bacteria. *P. fluorescens* was maintained in nutrient agar slants (Difco) at 4° C. *Escherichia coli* B #63X152 and *Bacillus subtilis* #64X395 were obtained from the Laboratory of Streptococcal Diseases, National Institute of Allergy and Infectious Diseases, and *P. aeruginosa*, isolated from a patient, was furnished by the Clinical Pathology Department, National Institutes of Health. These species were cultured as described below for *P. fluorescens*, but were incubated at 37° C. instead of 26° C. since they grow best at this temperature.

Preparation of the anti-trypanosome factor (ATF). The factor was prepared according to the scheme shown in the flow diagram. Sterilized water was used throughout and gentamycin was added to all buffers at a concentration of 50 μg/ml. All filtrates were checked for sterility by incubation in blood agar and nutrient broth. Sephadex was equilibrated with 120 mM Tris-HCl, 0.15 M NaCl, pH 7.4. Further analysis of the ATF was made with polyacrylamide (10%) gel electrophoresis (SDS-mercaptoethanol) and staining with Coomasie blue and the periodic acid-Schiff reaction.

Trypanosome-bacterium interaction (TB). Two methods were used: (1) microscopic examination and (2) readings of turbidity changes (Klett-Summerson spectrophotometer at 540 nm). For microscopic examination, duplicates (0.15 and 0.30 ml) of a parasite buffer suspension containing at least $2.5 \times 10^7$/ml were mixed with 0.30 ml of the Pseudomonas factor (equivalent to at least 1.0 mg protein/ml). Observations were made immediately, after 10 minutes, and after 12 and 24 hours. The mixtures were maintained at 4° C. Observations were based on the examination of the TB mixtures for one minute. To check for the lytic effect spectrophotometrically, turbidity readings were made every 5 minutes following the addition of ATF-I or II to the parasite buffer suspension. RESULTS: Assays performed with extracellular filtrates obtained from other bacterial species (shown below) were negative with the notable exception of *P. aeruginosa* which produced a lytic effect resembling that of *P. fluorescens*. as shown by Meinke and Berk Proc. Soc. Exper. Biol. Med., 135:360-363, 1970. *P. aeruginosa*, however, also proved toxic to mice, killing the animals in 24 to 48 hours. All the flagellated species tested, other than the Tulahuen strain; i.e., strains House 510 and House 11 of *T. cruzi*, the African trypanosomes, *T. rhodesiense* and *T. equiperdum*, and *L. brasiliensis* were equally sensitive to the ATF.

| IN VITRO EXPERIMENTS WITH ATF-II | | |
|---|---|---|
| | Effect After | |
| Species | 10 Minutes | 24 Hours |
| *Bacillus subtitlis*[1] | No change | Contracted shapes |
| *Escherichia coli*[1] | No change | No change |
| *Escherichia coli*[2] | No change | No change |
| *Pseudomonas aeruginosa*[1] | Immobilization | Lysis |
| *Salmonella typhimurium* (B25624)[2] | No change | No change |
| *Salmonella typhosa* (10310)[2] | No change | No change |
| *Serratia marcescens* (B115512)[2] | No change | No change |
| *Pseudomonas fluorescens* | 100% contracted shapes after | Lysis |

-continued

IN VITRO EXPERIMENTS WITH ATF-II

| Species | Effect After | |
|---|---|---|
| | 10 Minutes | 24 Hours |
| | 8 hours | |

[1]300 μg of crude protein
[2]300 μg of lipopolysaccharide

EXAMPLE 2

In vivo studies indicated that in 20-gram male Swiss mice which received intramuscularly a total of 6 mg of the active fraction over a period of 58 days following the intraperitoneal inoculation of 1,000 parasites, the progression of the parasitemia was stopped. 32 flagellates per 10 microscopic fields was the highest parasite count observed. The marked parasite multiplication and necrotic changes commonly produced in liver and spleen by this reticulotropic strain were also absent in treated animals which recovered from the infection. Studies of tissues from animals killed after various intervals of treatment indicated that, although some parasites were able to penetrate and multiply, since some organisms and histological changes were observed 13 days after inoculation, the usual progression of the infection was controlled, leading to the disappearance of the tryponastigotes from the blood stream (30 negative microscopic fields) and restoration of normal tissue architecture. All untreated infected animals and other untreated infected animals which were injected with buffer instead of the ATF died 13 to 21 days after inoculation.

It appears that the Pseudomonas factor could interrupt the infection in the following ways: (1) the parasites were so altered during the continued course of treatment that they could not always penetrate the susceptible tissues, (2) lysis in the blood stream led to a marked reduction of the number of trypomastigotes available for penetration, and (3) the ATF-II is believed to have also altered the tissue stages of the parasite, consequently interrupting the normal amastigotetrypomastigote cycle.

The lytic effect of an extracellular substance from *Pseudomonas fluorescens* on trypomastigotes (Tulahuen strain) of *Trypanosoma cruzi* is found above. An active fraction (ATF-II) recovered from the Pseudomonas culture filtrates, of an approximate molecular weight of 1,000, was very active against the flagellates and well tolerated in mice.

We claim:

1. An anti-trypanosome product prepared by the process of fractionating the supernatants of *Pseadomonas fluorescens* bacteria by filtering said supernatants through a filter having a pore size of 0.45 μm into fractions with molecular weight approximately 1,000 (ATF-II) and molecular weight greater than 20,000.

2. The process of claim 1 further comprising the steps of lyophiling and dialyzing the ATF-II fraction; reconstituting said ATF-II fraction in buffered distilled water at pH 8.

3. A composition for treating Chagas' disease in mice comprising 100-6000/μg of anti-trypanosome factor-II of claim 1, suspended in buffered water at pH 8 to which 50 μg/ml of gentamycin has herein added.

4. A method of treating Chagas' disease in mice comprising injecting intramuscularly into mice an effective amount of the composition of claim 3.

* * * * *